United States Patent [19]
Alphin et al.

[11] 3,993,767

[45] Nov. 23, 1976

[54] COMPOSITIONS TO SUPPRESS GASTRIC BLEEDING IN INDOMETHACIN AND PHENYLBUTAZONE THERAPY

[75] Inventors: Reevis Stancil Alphin; David Andrew Droppleman, both of Richmond, Va.

[73] Assignee: A. H. Robins Company, Incorporated, Richmond, Va.

[22] Filed: Nov. 18, 1975

[21] Appl. No.: 633,043

[52] U.S. Cl. .............................. 424/272; 424/273; 424/274
[51] Int. Cl.$^2$ ................. A61K 31/40; A61K 31/42; A61K 31/415
[58] Field of Search ................... 424/272, 274, 273

[56] References Cited
FOREIGN PATENTS OR APPLICATIONS
2,121,529   8/1972   France

OTHER PUBLICATIONS

Modell, Drugs In Current Use & New Drugs, 1973, p. 80.

Primary Examiner—Stanley J. Friedman

[57] ABSTRACT

Methods of treating symptomatic conditions of inflammation due to chronic and acute rheumatic and degenerative joint disease with a combination of indomethacin or phenylbutazone and a phenoxymethyl-2-oxazolidinone resulting in beneficial reduction in side effects of ulceration and bleeding in the lower intestinal tract normally associated with indomethacin and phenylbutazone and compositions containing the combination are disclosed.

13 Claims, No Drawings

COMPOSITIONS TO SUPPRESS GASTRIC BLEEDING IN INDOMETHACIN AND PHENYLBUTAZONE THERAPY

BACKGROUND OF THE INVENTION

This invention relates to novel methods, combinations, and compositions for controlling inflammation in the relief of symptomatic, chronic and acute rheumatic conditions. More particularly, the invention relates to combinations and compositions of indomethacin or phenylbutazone and phenoxymethyl-2-oxazolidinones and methods of using them to ameliorate the undesirable side effects of indomethacin or phenylbutazone in the gastrointestinal tract.

Indomethacin and phenylbutazone are widely used for the therapy of inflammatory conditions associated with rheumatic diseases and/or arthritis. However, certain undesirable side effects are associated with the use of indomethacin and phenylbutazone in the gastrointestinal region, among which side effects are bleeding, ulceration, perforation of the intestines and occasionally death. The need to overcome the irritation, particularly in the lower gastrointestinal tract, caused by indomethacin and phenylbutazone is a matter of urgent concern, inasmuch as the walls of the intestine in the lower region are relatively thin and perforation may occur suddenly and without warning. The method of the present invention, having suitably overcome, by remedial action, the severe manifestation of ulceration and perforation in the lower GI tract normally associated with indomethacin and phenylbutazone therapy, is highly suited to the treatment of the symptomatic inflammatory effect in mammals and humans of diseases such as gouty arthritis, bursitis, rheumatoid arthritis, rheumatoid spondylitis, osteoarthritis and the like.

Indicative of the state of the art have been attempts to find combinations which would allow administration of indomethacin or phenylbutazone for their full therapeutic effect as anti-inflammatory drugs. Certain steroids such as spirolactone have shown protection against intestinal ulcers caused by indomethacin in rats [Can. J. Physiol. Pharmacol. 1969, 47 (12) 981–3]. Coprecipitates of lignosulfonate or tannic acid with indomethacin or phenylbutazone have shown reduced irritation on the stomach tissue of cats. [C. A. 78, P102009n and C. A. 79, P9873]. Pro-Bathine which is ammonium (2-hydroxyethyl)-diisopropylmethylbromide, xanthine-9-carboxylate has shown reduced ulceration caused by indomethacin in the rat stomach [Arch. Int. Pharmacodyn. 191, 370–377 (1971)].

Cyclobenzaprine has been combined with indomethacin or phenylbutazone for muscle relaxant effects (French Pat. No. 2,121,529). The dosages of indomethacin and phenylbutazone required are alleged to be less than the dosages normally required for effectiveness, and because less of these drugs are used side effects are reduced. In the instant invention these drugs are the phenoxymethyl-2-oxazolidinones which are administered for their anti-inflammatory effects act in the presence of normal dosage amounts of indomethacin and phenylbutazone to reduce incidence of intestinal bleeding, ulceration, perforation and death. Furthermore, muscle relaxation due to the phenoxymethyl-2-oxazolidinones in the combinations and compositions of this invention is not a prerequisite for accomplishing the reduction of side effects as the method of the invention has been demonstrated in animals at dosages which did not cause muscle relaxation to occur.

SUMMARY OF THE INVENTION

The present invention provides novel compositions and methods of using said compositions for treating mammals, including humans, for inflammation associated with rheumatic-arthritic conditions. The methods comprise administering combinations of indomethacin or phenylbutazone and certain phenoxymethyl-2-oxazolidinones. We have discovered that when certain phenoxymethyl-2-oxazolidinones are used in combination with indomethaccin or phenylbutazone the incidence of ulceration and danger of perforation in the lower gastrointestinal tract where tissue walls are thinnest are greatly reduced. For example, ulceration is practically eliminated in the critical area of the jejunum of dogs and is reduced overall from the jejunum through the colon in about 50% of dogs. In general the method of this invention comprises administering normally effective daily dosages of from about 0.5 to about 3 mg/kg indomethacin or from about 1 to about 10 mg/kg phenylbutazone to control the inflammation in the subject and concomitantly administering from about 1 to about 30 parts by weight of a phenoxymethyl-2-oxazolidinone per part of indomethacin or phenylbutazone. Preferably from about 1 to about 10 parts by weight of the phenoxymethyl-2-oxazolidinone per part of indomethacin or phenylbutazone are administered. Preferably the phenoxymethyl-2-oxazolidinone is also administered in multiple daily dosages beyond the time the combination is administered as a protective measure against delayed ulcerative effects of indomethacin or phenylbutazone which delay may last up to five days depending upon the amount administered. The phenoxymethyl-2-oxazolidinone may be administered orally in intimate or physical mixture with indomethacin and phenylbutazone with or without adjuvants or carriers in unit dosage form, or it may be administered separately with or without adjuvants or carriers in a separate dosage form. The important requisite is that the phenoxymethyl-2-oxazolidinone be administered concomitantly in a manner such that blood levels of the phenoxy-2-oxazolidinone are generally sufficiently high to provide protection during the period of time indomethacin or phenylbutazone is a potential threat to the integrity of the lower intestinal tract wall. The invention is, however, also concerned with the compositions containing phenoxymethyl-2-oxazolidinones in effective proportions to indomethacin and phenylbutazone for ameliorating ulceration and which may be administered in unit dosage form during the period of time necessary to administer the anti-inflammatory drugs. In general, from about 1 to about 30 parts of phenoxymethyl-2-oxazolidinone per part by weight of indomethacin or phenylbutazone is necessary in the composition for effective remedial control of side effects in the lower gastrointestinal tract.

The phenoxymethyl-2-oxazolidinones useful in this invention have the formula:

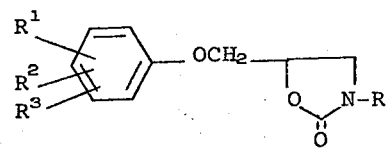

Formula I wherein;

R is selected from the group consisting of hydrogen or lower-alkyl having 1 to 4 carbon atoms, $R^1$ and $R^2$ each are selected from the group consisting of hydrogen, chlorine, bromine, fluorine, lower-alkyl, or lower-alkoxy, and $R^3$ is selected from the group consisting of hydrogen, lower-alkyl, chlorine, bromine or fluorine.

The phenoxymethyl-2-oxazolidinones of Formula I are prepared using the methods disclosed in U.S. Pat. Nos. 3,062,826; 3,062,827, 2,895,960; and 3,299,088, and Canadian Pat. No. 633,620.

The primary object of the present invention is to provide a method of treating inflammation with indomethacin or phenylbutazone in mammals and humans wherein the dangerous side effects of incidence of intestinal ulceration and perforation are minimized by concomitant administration of ulcer ameliorating phenoxymethyl-2-oxazolidinones.

Another object is to provide a method of treating inflammation with indomethacin or phenylbutazone wherein the incidence and severity of diarrhea and melena are decreased by concomitant or co-administration of phenoxymethyl-2-oxazolidinones.

A further object is to provide a method of reducing incidence of intestinal ulceration due to the after side effects of indomethacin and phenylbutazone by post treatment with certain phenoxymethyl-2-oxazolidinones.

A still further object is to provide pharmaceutical compositions comprising combinations of indomethacin or phenylbutazone and phenoxymethyl-2-oxazolidinones in physical combination with acceptable carriers therefor in unit dosage forms for co-administration which are useful for treating inflammation with reduced incidence of harmful side effects.

Another object of this invention is to provide systemic protection to the intestinal mucosa of mammals resulting from indomethacin or phenylbutazone therapy by administering phenoxymethyl-2-oxazolidinones during and following said therapy with indomethacin or phenylbutazone.

Still other objects will occur to one skilled in the art from the description which follows and the appended claims.

DETAILED DESCRIPTION OF THE INVENTION

According to the method of this invention which comprises administration of a combination of indomethacin or phenylbutazone and a phenoxymethyl-2-oxazolidinone selected from among those of Formula I, symptomatic relief of inflammation accompanying rheumatoid and degenerative joint disease is obtained with reduced side effects, particularly in the critical area of the lower GI tract.

Included among the phenoxymethyloxazolidinones of Formula I useful in the practice of this invention are:
5-(3,5-dimethylphenoxymethyl)-2-oxazolidinone,
5-(2,4-dichlorophenoxymethyl)-2-oxazolidinone,
5-(3,5-dimethylphenoxymethyl)-3-ethyl-2-oxazolidinone,
5-(3-chlorophenoxymethyl)-2-oxazolidinone,
5-(4-chlorophenoxymethyl)-2-oxazolidinone,
5-(3-bromophenoxymethyl)-2-oxazolidinone,
5-(3-fluorophenoxymethyl)-2-oxazolidinone,
5-(3-chloro-2-methylphenoxymethyl)-2-oxazolidinone,
5-(4-chlorophenoxymethyl)-3-ethyl-2-oxazolidinone,
5-(3-chloro-6-toloxymethyl)-2-oxazolidinone,
5-(2,3,5-trimethylphenoxymethyl)-2-oxazolidinone,
5-(4-chloro-3-methylphenoxymethyl)-2-oxazolidinone,
5-(4-bromophenoxymethyl)-3-ethyl-2-oxazolidinone,
5-(3-methyl-4-chlorophenoxymethyl)-3-ethyl-2-oxazolidinone,
5-(3-methyl-4-chlorophenoxymethyl)-2-oxazolidinone,
5-(3-chloro-6-methylphenoxymethyl)-2-oxazolidinone,
5-(2-methoxyphenoxymethyl)-3-butyl-2-oxazolidinone,
5-(2-methoxyphenoxymethyl)-3-isopropyl-2-oxazolidinone,
5-(2,6-methoxyphenoxymethyl)-2-oxazolidinone,
5-(3-chloro-6-methoxyphenoxymethyl)-2-oxazolidinone.

Metaxalone (5-(3,5-dimethylphenoxymethyl)-2-oxazolidinone) represents a preferred embodiment of Formula I.

EXAMPLE 1

Effect of Metaxalone on Gastrointestinal Toxicity of Indomethacin in Dogs

The protective and remedial effect of metaxalone against the systemic gastro-intestinal toxicity produced by indomethacin was studied in 10 mongrel dogs ranging in weight from 6.7 to 10.8 kg. Each dog was dosed daily with a single dose of 5 mg/kg indomethacin in capsule form. Five of the dogs were treated with 100 mg/kg metaxalone given orally in gelatin capsules twice daily. All animals were observed for changes in food consumption and body weight and for evidence of melena. Blood samples (0.5 ml.) were drawn three times a week and hemoglobin values determined to indicate the presence of blood loss. Hemoglobin was determined by the cyanmethemoglobin method. At necropsy the entire gastrointestinal tract was excised and examined for mucosal erosions and ulcers. Gastrointestinal damage was evaluated subjectively by an arbitrary grading system on a blind basis by a pharmacologist and recorded as the ulcer index. The grading system used is a modification of that described by Placer, Roubal and Vocac, "The Action of Gastric Mucosa and Some Sulfonated Compounds on the Development of Experimental Gastric Ulcers In Rats," Review of Czechoslovakian Medicine IV p. 111, 1958. On day eleven all surviving dogs were sacrificed. No significant differences were observed between dogs receiving only indomethacin (control) and dogs receiving metaxalone in addition to indomethacin (treated) as regards food consumption, body weight, blood hematocrit or hemoglobin, although the total decrease in these values was considerable. The greatest differences observed were in the amount of gastrointestinal damage and survival rate.

The following Table 1 shows the extent of damage of various segments of the gastrointestinal tract for control and treated dogs expressed as an ulcer index. The least protection due to metaxalone administration was seen in the antrum of the stomach and the duodenal bulb. Maximum protection was observed in the jejunum. In the treated group of dogs, however, there was a 50% reduction of ulceration in the lower GI tract, i.e., jejunum, illeum and colon; there was an overall reduction in ulceration of 27%.

Table 1

Effect of Metaxalone on Gastrointestinal Toxicity of Indomethacin in Dogs - Average Ulcer Index

| Group | Fundus | Antrum | Pyloric Duodenal Junction | Duodenal Bulb | Duodenum |
|---|---|---|---|---|---|
| Controls *(Indomethacin)[a] | 13 | 34 | 14 | 6 | 9 |
| Treated *(Indomethacin[a] and Metaxalone)[b] | 9 | 34 | 11 | 16 | 1 |
| % Change | −30.8 | 0 | −21.4 | +166.7 | −88.9 |

| Group | Jejunum | Proximal Ileum | Mid Ileum | Terminal Ileum | Colon |
|---|---|---|---|---|---|
| Controls *(Indomethacin)[a] | 16.0 | 21 | 23 | 30 | 2 |
| Treated *(Indomethacin)[a] and Metaxalone)[b] | 0 | 14 | 18 | 19 | 1 |
| % Change | −100.0 | −33.3 | −21.7 | −36.7 | −50.0 |

*Average Ulcer Indeces.
Dosage: [a]5 mg/kg indomethacin in capsule form, p.o.
[b]100 mg/kg metaxalone twice daily, p.o.

The survival times of all dogs for the eleven days are shown in Table 2. The first control animal died on day six, four days before the first treated dog. On day nine only 20% of the control group remained as compared to 100% of the treated group. Survivors in the treated group decreased to 60% by day eleven.

Table 2

Effect of Metaxalone on Survival Rate of Indomethacin Dosed Dogs

| | Percent Surviving | |
|---|---|---|
| Day | Control (Indomethacin) | Treated (Indomethacin and Metaxalone) |
| 1−5 | 100 | 100 |
| 6 | 80 | 100 |
| 7 | 80 | 100 |
| 9 | 20 | 100 |
| 10 | 20 | 60 |
| 11 | 20 | 60 |

In addition to a reduction in ulceration and the increase of survival rate, the treated group exhibited a decrease in both onset and severity of diarrhea and melena.

EXAMPLE 2

Effect of Metaxalone on Gastro-intestinal Toxicity of Indomethacin and Phenylbutazone in Rats The protective effect of metaxalone on the gastrointestinal toxicity of indomethacin and phenylbutazone was studied in rats. Female Sprague Dawley rats weighing 160–190 g. were used. Animals had access to food and water at any time.

In Experiment I, metaxalone was evaluated for protective effect against the intestinal toxicity of indomethacin at lethal dose range ($LD_{100}$). Three groups of rats were used. The first group (13 rats) received saline (4 ml/kg, p.o.). The second group (21 rats) and the third group (20 rats) received a single dose of indomethacin (20 mg/kg, p.o.). Thirty minutes prior to indomethacin administration the second group received acacia (4 ml/kg, p.o. of a 5% suspension) as control and the third group was given metaxalone (200 mg/kg, p.o.) in 4 ml/kg of a 5% suspension of acacia. On the subsequent eight days, group 2 received acacia and group 3 received metaxalone in acacia suspension twice daily. The treatment was discontinued after eight days and the surviving animals observed for several weeks for delayed death.

In a second experiment metaxalone was evaluated for antagonism to the intestinal toxicity of phenylbutazone. Two groups of 15 rats each were used. One group received phenylbutazone (150 mg/kg, p.o.) and acacia (4 ml/kg, p.o. of a 5% suspension). The second group received phenylbutazone (150 mg/kg, p.o.) and metaxalone (200 mg/kg, p.o.) in acacia suspension (4 ml/kg). Both groups were treated twice daily. All animals were sacrificed on the fifth day and examined for gastrointestinal damage.

The results of the effects of metaxalone on the intestinal toxicity of indomethacin is shown in Table 3. None of the animals treated with metaxalone died, whereas 86% of the acacia control treated animals died within three weeks. Several of the deaths were delayed. As can be readily concluded from the survival data, the method of the invention involves possible short range treatment with even up to otherwise lethal doses of indomethacin.

Table 3

Effect of Metaxalone on Indomethacin-Induced Toxicity In Rats

| Group | No. Rats | No. Deaths | % Mortality |
|---|---|---|---|
| Normal (no treatment) | 13 | 0 | 0 |
| Acacia[1] | 21 | 18 | 86 |
| Treated[2] | 20 | 0 | 0 |

[1]Acacia (4 ml/kg, p.o. of a 5% suspension + Indomethacin (20 mg/kg, p.o.).
[2]Metaxalone (200 mg/kg, p.o.) + Indomethacin (20 mg/kg, p.o.).

In Table 4, the effects of metaxalone on the intestinal toxicity of phenylbutazone are shown. Sixty-three percent of the untreated rats had gastrointestinal ulceration. Forty percent of the rats treated with metaxalone had ulceration. Based on an arbitrary scoring system of 0 − 40, the control index was 21.3 as compared to an index of 8.3 in the metaxalone treated group.

Table 4

Effect of Metaxalone on Phenylbutazone-Induced Toxicity in Rats

| Treatment | No. Rats | Gastrointestinal Ulcer Index | % Protection |
|---|---|---|---|
| Acacia[1] | 15 | 21 | — |
| Metaxalone[2] | 15 | 8 | 61 |

[1]Acacia (4 ml/kg, p.o. of a 5% suspension) + Phenylbutazone (150 mg/kg, p.o.).
[2]Metaxalone (200 mg/kg, p.o.) + Phenylbutazone (150 mg/kg, p.o.).

Table 5

Activity of Indomethacin and Metaxalone Alone and in Combination in Adjuvant-Induced Arthritic Rats Using A Therapeutic Dosing Regimen

| Compound | Indomethacin Dose mg/kg Orally | No. Rats Surviving | Edema ml ± S.D. Days 18–29 Injected Foot | Days 18–29 Uninjected Foot | Days 18–36 Injected Foot | Days 18–36 Uninjected Foot |
|---|---|---|---|---|---|---|
| Indomethacin | 10[2] | 0/6 | All Animals Died by Day 23 | | | |
|  | 4[2] | 6/7[3] | −1.3 ± 0.27[1] | −0.6 ± 0.40[1] | −1.6 ± 0.32[1] | −0.7 ± 0.43[1] |
|  | 1[2] | 8/8 | −1.2 ± 0.38[1] | −0.6 ± 0.22[1] | −1.6 ± 0.36[1] | −0.7 ± 0.30[1] |
|  | 0.1[2] | 8/8 | −0.1 ± 0.33 | −0.1 ± 0.36[1] | −0.6 ± 0.38[1] | −0.2 ± 0.45[1] |
|  | 0.01[2] | 8/8 | +0.6 ± 0.54 | +0.8 ± 0.40 | +0.6 ± 0.86 | +0.8 ± 0.63 |
| Indomethacin + 200 mg/kg Metaxalone twice daily | 10 | 3/8[4] | −1.3 ± 0.47[1] | −0.4 ± 0.06[1] | −1.5 ± 0.42[1] | −0.5 ± 0.10[1] |
|  | 4 | 8/8 | −0.9 ± 0.35[1] | −0.6 ± 0.31[1] | −1.1 ± 0.31[1] | −0.7 ± 0.29[1] |
|  | 1 | 8/8 | −0.7 ± 0.36[1] | −0.3 ± 0.36[1] | −1.0 ± 0.54[1,6] | −0.4 ± 0.44[1] |
|  | 0.1 | 8/8 | 0 ± 0.30 | +0.4 ± 0.51 | 0 ± 0.39[1,6] | +0.3 ± 0.58[1] |
|  | 0.01 | 8/8 | +0.1 ± 0.41 | +0.2 ± 0.30[1] | +0.3 ± 0.52 | +0.2 ± 0.40[1,6] |
| Metaxalone 200 mg/kg[5] Control | none | 8/8 | +0.2 ± 0.21 | +0.4 ± 0.27 | +0 ± 0.35 | +0.3 ± 0.25 |
| 0.5% Tween 80 | 5 mg/kg[5] |  | +0.6 ± 0.87 | +0.8 ± 0.77 | +0.8 ± 1.05 | +1.1 ± 1.07 |

[1]P <.05 from control as determined by the Dunnett t-test.
[2]Received also 5 ml/kg of 0.5% Tween 80 in the morning.
[3]Two animals died; one death was due to the compound.
[4]Five animals died due to drug effect by day 26.
[5]Administered twice daily.
[6]P <.05 from respective indomethacin-treated group as determined by multivariate analyses of covariance.

Effect of Metaxalone on the Anti-Inflammatory Activity and Toxicity of Indomethacin In Adjuvant-Induced Arthritic Rats The effect of metaxalone was studied extensively in rats for its effect on the anti-inflammatory activity of indomethacin over a dosage range for indomethacin of 0.01 to 10 mg/kg. As the test progressed toxicity comparisons were also noted.

The method used for the adjuvant-induced arthritis test was a modification of the method of Walz, D. T., et al., J. Pharmacol. 178: 223–321 (1971) which consisted of a therapeutic rather than a prophylactic dosing regimen used by Walz. Female Charles River Lewis Wistar rats weighing 150 to 200 grams were used. On day 0 a tattoo was made on each leg at the point where the achilles tendon entered the gastrocnemius muscle. This served as a reference point for measuring limb volume plethysmographically. Approximately three hours later 0.05 ml. of a suspension of 1.5% *Mycobacterium butyricum* (sonified) in mineral oil was injected into the subplanter surface of the right hind foot. On day 18 the limb volumes of both feet were determined.

Those animals with significant swelling of the uninjected foot were randomized by block design into groups of eight (See Table 5). Compounds were suspended or dissolved in 0.5% Tween 80 and administered by gavage. Sonification was used to reduce the particle size or to facilitate solubilization. The total volume administered at any one time was 5 ml/kg. The animals were weighed on Mondays, Wednesdays and Fridays to determine the dosage. Compounds were administered daily five days a week according to the following schedule. Animals receiving indomethacin alone received 5 ml/kg Tween 80 vehicle at 9:30 a.m. and the anti-rheumatic drug in 5 ml/kg Tween 80 at 4:00 p.m. Those animals receiving the metaxalone and indomethacin received 200 mg/kg metaxalone in 5 ml/kg Tween 80 at 9:30 a.m. and 200 mg/kg metaxalone at 4:00 p.m. The latter was followed immediately by the specified amount (See Table 5) of indomethacin in 2.5 ml/kg Tween 80. Another group received 200 mg/kg of metaxalone twice a day each time in 5 ml/kg Tween 20. Positive and negative control groups received the vehicle in the same manner as all the treated groups. On days 29 and 36 the edema of the injected and uninjected feet and changes in body weight were determined by difference. Significance of the data was determined by the Dunnett's t-test, Dunnett, C. W., J. Am. Statistical Association 50, pp 1096–1121 (1955), using either the raw or logtransformed data. The method of Bliss, C. W., Vitamin Methods, ed. by P. Gyorgy, Vol. 11, Academic Press, New York, 1951, was used to determine potency and 95% confidence limits.

Multivariate analyses of covariance indicates a significant dose-drug interaction at $P < .025$. Therefore, the two treatments were compared in a univariate manner at each dose. The analysis indicated that metaxalone at 200 mg/kg orally twice daily reduced the edema of the injected and uninjected feet of arthritic rats. When given at this dose with indomethacin, metaxalone did not significantly antagonize the suppression by 0.1, 1, and 4 mg/kg orally of indomethacin on the edema of the uninjected feet of arthritic rats. However, metaxalone significantly enhanced the effect of 0.01 mg/kg of the anti-rheumatic drug on the edema of uninjected foot. In contrast, metaxalone significantly reduced the effect of 0.1 and 1 mg/kg of indomethacin on the edema of the injected foot. Since the edema of the uninjected foot of adjuvant arthritic rats represents the systemic manifestations of the disease, metaxalone did not overall significantly alter the anti-inflammatory activity of indomethacin. At 200 mg. metaxalone/kg administered twice daily the rats exhibited no visible evidence of muscle relaxation.

Weight loss as a measure of growth is another manifestation on this disease in rats and this is reversed as the disease is suppressed by non-steroidal anti-inflammatory drugs such as indomethacin. The arthritic animals treated with the combination of indomethacin and metaxalone showed growth similar to those receiving the corresponding dose of indomethacin alone, Table 6.

Observations on toxicity as evidenced by death of rats on day-after-day administration of indomethacin or a combination of 4–10 mg/kg indomethacin and metaxalone indicated that metaxalone ameliorated the toxic effects of indomethacin although this was not the purpose of the study. At the 10 mg/kg per day level all animals were dead after 5 days treatment with indomethacin, whereas ⅝ survived when metaxalone was also administered. Those animals which died showed no necropsy evidence of gastrointestinal toxicity. At the 4 mg/kg indomethacin level, one rat died showing gastrointestinal lesions contrasted to no deaths for rats administered metaxalone.

Table 6

Effect of Indomethacin and Metaxalone Alone and in Combination on the Growth of Adjuvent-Induced Arthritic Rats Using a Therapeutic Dosing Regimen

| Compound | Indomethacin Dose mg/kg | No Rats | Growth g ± S.D. Days 18–29 | Days 18–36 |
|---|---|---|---|---|
| Indomethacin | 4 | 6 | +30 ± 7.9[1] | +43 ± 11.6[1] |
|  | 1 | 8 | +20 ± 6.4[3] | +34 ± 7.6[1] |
|  | 0.1 | 8 | +12 ± 8.2 | +25 ± 8.9 |
|  | 0.01 | 8 | +17 ± 7.7 | +29 ± 6.2 |
| Indomethacin | 10 | 3 | +31 ± 2.5[1] | +44 ± 2.1[1] |
| + | 4 | 8 | +24 ± 7.6[1] | +38 ± 6.0[1] |
| 200 mg/kg |  |  |  |  |
| Metaxalone | 1 | 8 | +20 ± 6.7[1] | +30 ± 13.0 |
| twice daily | 0.1 | 8 | +17 ± 7.2 | +30 ± 6.6 |
|  | 0.01 | 8 | + 9 ± 3.7 | +21 ± 5.5 |
| Metaxalone 200 mg/kg Control (Positive) | none | 8 | +13 ± 5.2 | +26 ± 9.9 |
| 0.5% Tween 80 Control (Negative) | 5 ml/kg | 8 | +10 ± 8.9 | +20.6 ± 9.0 |
| 0.5% Tween 80 | 5 ml/kg | 8 | +14 ± 4.7 | +26 ± 4.1[2] |

[1]$P < .05$
[2]Two animals were lost during the course of the experiment
[3]$P < .05$ when data was log-transformed

METHODS OF ADMINISTRATION

The combination of indomethacin or phenylbutazone with the phenoxymethyl-2-oxazolidinones useful in this invention is administered to a variety of mammals including humans, dogs, cats and horses suffering from inflammatory symptoms associated with diseases hereinabove mentioned with greatly reduced side effects in ulceration of the lower intestines. The phenoxy-2-oxazolidinones may be administered separately from the indomethacin and phenylbutazone or together in a physical mixture which may or may not be intimately mixed. When administered separately, either of the anti-inflammatory agents or the phenoxymethyl-2-oxazolidinones may be given orally simultaneously or at different times during the day. The oxazolidinones may alternately be given intravenously in a satisfactory solvent such as dimethylisosorbide. Generally, however, in order to insure that administration of the oxazolidinones is not neglected, the surest procedure is to administer the combination orally as a mixture or layered tablet and therefore this procedure and a composition based on the combination represent preferred embodiments of the invention. The protective, remedial and ameliorating effect of the oxazolidinones is maximized when administration of the therapeutic amounts of the oxazolidinones is continued beyond termination of administration of indomethacin and phenylbutazone combinations or compositions with the oxazolidinones. It is therefore advisable generally to continue administration of the oxazolidinones in multiple daily dosages for periods up to several days beyond termination of administration of indomethacin and phenylbutazone. Generally, subjects receiving maximum or larger doses on a mg/kg basis will receive greater benefit by the continued treatment with the oxazolidinones beyond administration of indomethacin and phenylbutazone for their anti-inflammatory effects.

According to the present invention as disclosed hereinabove, it has been found that irritation of the lower intestinal tract, which is a primary adverse side effect to the administration of indomethacin or phenylbutazone for their anti-inflammatory effect in mammals, is minimized when the phenoxymethyl-2-oxazolidinones described hereinabove are also administered in a ratio of in parts by weight of about 1 to about 30 parts per part of indomethacin or phenylbutazone, preferably about 1 to 10 parts per part of said anti-inflammatory agents. The amount of indomethacin contained in the combinations and compositions of this invention administered on a daily basis varies from about 0.5 to 3 mg/kg body weight and the amount of phenylbutazone on a daily basis varies from about 1 to 10 mg/kg body weight. Thus, for example, on a daily basis, subjects receiving the combination at the highest preferred ratios of oxazolidinone to inflammatory agent at its upper dosage range, in the case of indomethacin therapy would receive on a daily basis 3 mg/kg indomethacin and 30 mg/kg of the oxazolidinone and in the case of phenylbutazone therapy would receive on a daily basis 10 mg/kg phenylbutazone and 100 mg/kg oxazolidinone the phenoxymethyl-2-oxazolidinone in the range of from 1 to 300 mg/kg. In general, post-treatment with the oxazolidinones may continue at the same dosage rate as oxazolidinone present in the combination.

The choice of ratio within the range of about 1 to about 30 parts by weight of oxazolidinones of Formula I to anti-inflammatory agent used in any combination or composition on a variety of subjects will depend somewhat on the species of chemical of Formula I used. It will also depend on such factors as sensitivity of the subject to indomethacin or phenylbutazone and to species of mammal under treatment.

When the combinations of this invention are administered as a composition the mixture will be in a form suitable for oral use, for example, as tablets, hard or soft capsules, aqueous or oily suspensions, dispersible powders or granules, emulsions, hard or soft capsules or syrups or elixirs. The compositions may be prepared according to any known method for the manufacture of pharmaceutical compositions and such compositions may contain one or more agents selected from sweetening agents, flavoring agents, preserving agents and coloring agents in order to provide a pharmaceutically elegant and palatable preparation. Tablets contain the active ingredient in admixture with non-toxic pharmaceutically acceptable excipients which are suitable for the manufacture of tablets. These excipients may be, for example, inert diluents such as lactose, calcium or sodium phosphate, calcium or sodium carbonate, granulating and disintegrating agents such as maize, starch or alginic acid and its salts; binding agents, for example, starch, gelatin or acacia and lubricating agents, for example, magnesium stearate, stearic acid or talc. The tablets may be coated by known techniques to delay disintegration and absorption in the gastrointestinal tract and thereby provide a sustained action over a longer period. For example, monostearate or glyceryl distearate or a waxy material may be inclosed in hard gelatin capsules mixed therein with an inert solid diluent, for example, calcium carbonate, calcium phosphate, lactose, magnesium stearate or Kaolin, or in soft gelatin capsules which the active ingredient is mixed with a liquid carrier such as water or an oily medium, for example, vegetable oil or mineral oil.

Aqueous suspensions containing the combinations with excipients suitable for the manufacture of aqueous suspensions may be used. Suitable excipients are suspending agents, for example, sodium carboxyethylcellulose, methylcellulose, hydroxypropylmethylcellulose, sodium alginate, polyvinylpyrrolidone, gum tragacanth and acacia. Dispersing agents included may be naturally occurring phosphatides such as lecithin, condensation products of an alkalene oxide with fatty acids, for example, polyoxyethylene stearate, condensation products of ethylene oxide with long chain aliphatic alcohols, for example, heptadecaethyleneoxycetanol, condensation products of ethylene oxide with partial esters derived from fatty acids and a hexitol, for example, polyoxyethylene sorbitan, mono-oleate, or condensation products of ethylene oxide with partial esters derived from fatty acids and hexitol anhydrides, for example, polyoxyethylene sorbitan mono-oleate. The said aqueous suspension may also contain preservatives, for example, ethyl or n-propyl-p-hydroxybenzoate, coloring agents, flavoring agents, sweetening agents such as sucrose or saccharin.

Oily suspensions may be formulated by suspending the anti-inflammatory agent and the ulcer ameliorating agent, a phenoxymethyl-2-oxazolidinone in a vegetable oil, for example, a mineral oil, olive oil, coconut oil, or the like. The oily suspensions may contain a thickening agent such as wax or waxy alcohols. Flavoring and sweetening agents may be added to provide oral preparations which are palatable. Antioxidants such as ascorbic acid may be added as preservatives.

Dispersible powders and granules of anti-inflammatory agent and ameliorating agent suitable for preparation of oral dosage forms which are aqueous suspensions when water is added are provided when dispersing agents, suspending agents, and preservatives are admixed. Suitable dispersing agents and suspending agents are exemplified by those already mentioned above. Sweetening, flavoring and coloring agents may also be present.

Compositions containing the combinations of this invention may also be in the form of oil-in-water emulsions. The oily phase may be an edible oil such as the oils already described above for preparing oily suspensions. Suitable emulsifying agents may be naturally-occurring gums, for example, gum acacia or gum tragacanth, naturally-occurring phosphatides, for example, soy bean lecithin, and esters or partial esters derived from fatty acids and hexitol anhydrides, for example, sorbitan mono-oleate, and condensation products of the said partial esters with ethylene oxide, for example, polyoxyethylene sorbitan mono-oleate. The emulsions may also contain sweetening and flavoring agents.

Syrups and elixirs may be formulated with sweetening agents, for example, glycerol, sorbitol or sucrose. Such formulations may also contain a demulcent, a preservative and flavoring and coloring agents.

Alternately, according to the method of this invention, indomethacin or phenylbutazone in any form whatsoever and a phenoxymethyl-2-oxazolidinone of Formula I in any pharmaceutically suitable form whatsoever, such as tablets, capsules, suspensions, etc., may be administered concomitantly to a mammalian subject in need of treatment for inflammation for the purpose of ameliorating the undesirable side effects of indomethacin and phenylbutazone and the oxazolidinones in any pharmaceutically suitable form whatsoever, such as tablets, suspensions, capsules, may be administered following said concomitant treatment for ulcer ameliorating effects which occur due to the delayed action ulcerative effect of indomethacin and phenylbutazone. Solutions of phenoxymethyl-2-oxazolidinone in dimethylisosorbide may be prepared as described in U.S. Pat. No. 3,699,230 and administered when separate administration is the choice.

For veterinary oral use, the combination of indomethacin or phenylbutazone and phenoxymethyl-2-oxazolidinones of Formula I are conveniently prepared in tablets and capsules for unit dosage form of administration or in the form of powders and granules for admixing with food.

The tablets and capsules for veterinary use are generally prepared as described hereinabove. For pets such as dogs, the contained indomethacin will be about 2 to 10 mg/kg, or the contained phenylbutazone will be about 20 to 100 mg/kg; for horses 50 to 100 mg. indomethacin and 500–1000 mg. phenylbutazone.

The powders and granules for admixing with food are conveniently prepared as hereinabove described or in the form of a food premix. The food premix which can be quite dilute can comprise the combinations of this invention in admixture with edible pharmaceutical diluent such as starch, oatmeal, flour, calcium carbonate, talc, dried fish meal and dried meat meals. The powders or the prepared premix is then conveniently added to the regular feed, thereby providing the anti-inflammatory action of indomethacin or phenylbutazone without high incidence of perforated ulcer due to the ameliorating effects of the phenoxymethyl-2-oxazolidinone during the course of feeding. Granules of the combination of this invention may be prepared and coated for better reception in food by certain mammals which exhibit "finicky" eating habits such as cats and dogs.

The term "unit dosage form" as used in the specification and claims refers to physically discrete units suitable as unitary dosages for human subjects and animals, each unit containing a predetermined combination of anti-inflammatory agents, indomethacin or phenylbutazone and the ulcer ameliorating compound calculated to produce the desired therapeutic effect in association with the required pharmaceutical diluent, carrier or vehicle. The specifications for the novel preferred unit dosage forms wherein the said combination is used are dictated by and directly dependent on (a) the effective amount of anti-inflammatory component required for control of given symptoms and the sensitivity of the subject to the anti-inflammatory agent in the requirement of amount of ameliorating agent needed as disclosed hereinabove, (b) the limitations inherent in the art of compounding such active combinations for therapeutic use in humans and animals as disclosed in detail in this specification, these being features of the present invention. Examples of suitable unit dosage forms in accord with this invention are tablets, capsules, pills, powder pockets, granules, segregated multiples of any of the foregoing including the anti-inflammatory agents and the phenoxymethyl-2-oxazolidinones and other forms as herein described.

It will be understood, however, that the specific dose level for any particular patient will depend upon a variety of factors, including the activity of the anti-inflammatory agent employed and the ameliorating effect of the 2-oxazolidinone employed, the age, body weight, general health, sex, diet, mammalian specie, time of administration, and the severity of the particular disease undergoing therapy. In general, the dosage regimen in carrying out the methods of this invention is that which ensures maximum therapeutic response with maximum protection to the subject against side effects of the contained anti-inflammatory agent and thereafter is the minimum effective level which continues to provide relief. It will also be understood that while the combinations of the method of this invention are preferably prepared in unit dosage form containing both the ulcer ameliorating agent and the anti-inflammatory agent, the method of the invention also encompasses separate administration of these agents to subjects suffering from the symptomatic problems of arthritic type disease in unit dosage form of said agents. The method also encompasses continued administration of the ulcer ameliorating 2-oxazolidinone at least 1 to 5 days beyond the period of administration of the anti-inflammatory agent.

The compositions of the invention which are used in the preferred method of administering both anti-inflammatory agent and ulcer ameliorating agent in the same unit dosage form are illustrated by the following examples which are not intended to be limiting in any way.

Formulations

Example 1

(1) Capsules
Typical formulations for encapsulation are:

| | Per capsule, mg. |
|---|---|
| Indomethacin | 25.0 |
| Metaxalone | 250.0 |
| Lactose | 223.0 |
| Magnesium stearate | 4.3 |
| Total | 502.3 |

| | Per capsule, mg. |
|---|---|
| Phenylbutazone | 50.0 |
| Metaxalone | 500.0 |
| Magnesium stearate | 4.3 |
| Total | 554.3 |

Uniformly blend all ingredients and encapsulate the blend, preparing capsules with the mixtures.

Example 2

(2) Tablets
Typical formulations for tableting are:

| | Per tablet, mg. |
|---|---|
| Indomethacin | 25.0 |
| Metaxalone | 350.0 |
| Alginic acid | 20.0 |
| Calcium and ammonium alginate | 40.0 |
| Starch | 54.0 |
| Lactose | 75.0 |
| Magnesium stearate | 2.2 |
| Total | 546.2 |

| | Per tablet, mg. |
|---|---|
| Phenylbutazone | 50.0 |
| Metaxalone | 500.0 |
| Alginic acid and calcium ammonium alginate | 30.0 |
| Magnesium stearate | 3.2 |
| Starch | 40.0 |
| Lactose | 75.0 |
| Total | 728.2 |

The mixture, all except the magnesium stearate and one half of the calcium ammonium alginate, is blended and granulated with water and passed through a number eight mesh screen and the mixture dried 16 hrs. at 140° F.. The dried granulated material is then blended thoroughly with the remainder of the calcium ammonium alginate and magnesium stearate and tableted.

EXAMPLE 3

In another variation indomethacin tablets are prepared:

| | Per tablet, mg. |
|---|---|
| Indomethacin | 25.0 |
| Phenoxymethyl-2-oxazolidinone of Formula I | 250.0 |
| Lactose | 90.0 |
| Starch | 54.0 |
| Dicalcium phosphate | 172.0 |
| Calcium stearate | 2.2 |
| Total | 593.2 |

All ingredients are uniformly blended and granulated with water and the wet mass is passed through a number eight mesh screen. The wet granules are dried at 140°–160° for 16 hrs. using reduced pressure for final moisture removal.

EXAMPLE 4

3. Suspensions

A typical formulation for a suspension of indomethacin and metaxalone is:

| | Weight in grams |
|---|---|
| Indomethacin | 20.0 |
| Metaxalone | 200.0 |
| Glyceryl monostearate | 200.0 |
| Polysorbate 80 | .10 |
| Methylester of parahydroxybenzoate | .30 |
| Sodium chloride | 1.00 |
| Distilled water | 578.6 |
| | 1000.00 |

The glyceryl monostearate and Polysorbate 80 are dispersed at 65° C. in water containing the sodium chloride and methylparahydroxybenzoate, and the resulting mixture is sterilized by autoclaving. After the mixture has cooled to room temperature, powdered indomethacin and metaxalone are dispersed therein.

A suspension of phenylbutazone and metaxalone is similarly prepared.

What is claimed is:

1. The method of treating inflammatory conditions in mammals which comprises administering an effective amount of indomethacin or phenylbutazone and a phenoxymethyl-3-oxazolidinone of the formula:

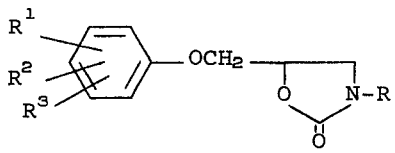

wherein;
R is selected from the group consisting of hydrogen or lower-alkyl having 1 to 4 carbon atoms,
$R^1$ and $R^2$ each are selected from the group consisting of hydrogen, chlorine, bromine, fluorine, lower-alkyl or lower-alkoxy, and
$R^3$ is selected from the group consisting of hydrogen, lower-alkyl, chlorine, bromine or fluorine.

2. The method of claim 1 wherein the phenoxymethyl-2-oxazolidinone is metaxalone.

3. The method of treating inflammatory conditions in mammals which comprises administering daily to a mammalian subject from 0.5 to 3.0 mg. indomethacin/kg of body weight and from about 1 to about 30 parts by weight per part by weight of said indomethacin of a phenoxy-2-oxazolidinone of the formula:

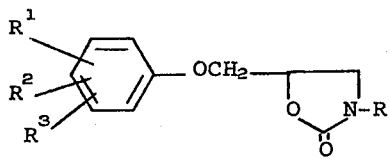

wherein;
R is selected from the group consisting of hydrogen or lower-alkyl having 1 to 4 carbon atoms,
$R^1$ and $R^2$ each are selected from the group consisting of hydrogen, chlorine, bromine, fluorine, lower-alkyl or lower-alkoxy, and
$R^3$ is selected from the group consisting of hydrogen, lower-alkyl, chlorine, bromine or fluorine.

4. The method of claim 3 wherein the phenoxymethyl-2-oxazolidinone is metaxalone.

5. The method of treating inflammatory conditions in mammals which comprises administering daily to a mammalian subject from 1 to 10 mg. phenylbutazone/kg of body weight and from about 1 to about 30 parts by weight per part by weight of said phenylbutazone of a phenoxymethyl-2-oxazolidinone of the formula:

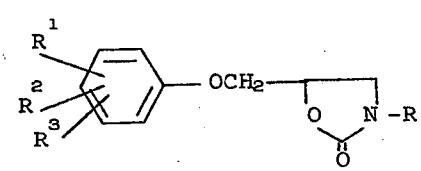

wherein;
R is selected from the group consisting of hydrogen or lower-alkyl having 1 to 4 carbon atoms,
$R^1$ and $R^2$ each are selected from the group consisting of hydrogen, chlorine, bromine, fluorine, lower-alkyl or lower-alkoxy, and
$R^3$ is selected from the group consisting of hydrogen, lower-alkyl, chlorine, bromine or fluorine.

6. The method of claim 5 wherein the phenoxymethyl-2-oxazolidinone is metaxalone.

7. The method of treating inflammatory conditions in mammals which comprises administering daily to a mammalian subject from 0.5 to 2 mg. indomethacin/kg of body weight or from 1 to 10 mg. phenylbutazone/kg body weight, and from about 1 to 30 parts by weight per part by weight of said indomethacin or phenylbutazone of a phenoxymethyl-2-oxazolidinone of the formula:

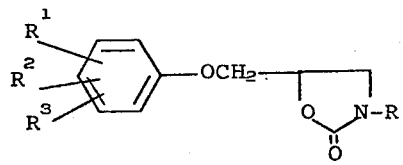

wherein;
R is selected from the group consisting of hydrogen or lower-alkyl having 1 to 4 carbon atoms,
$R^1$ and $R^2$ each are selected from the group consisting of hydrogen, chlorine, bromine, fluorine, lower-alkyl or lower-alkoxy, and
$R^3$ is selected from the group consisting of hydrogen, lower-alkyl, chlorine, bromine or fluorine,
and after termination of administration of said combination, continuing the administration of from 1 to 30 parts by weight of said phenoxymethyl-2-oxazolidinone for at least 1 to 5 days.

8. The method of claim 7 wherein the phenoxymethyl-2-oxazolidinone is metaxalone.

9. A pharmaceutical composition in unit dosage form adapted for administration to obtain an anti-inflammatory effect with minimal side effects comprising (a) per unit dosage an anti-inflammatory effective amount of indomethacin or phenylbutazone and from about 1 to 30 parts by weight, based on said indomethacin or phenylbutazone of a phenoxymethyl-2-oxazolidinone of the formula:

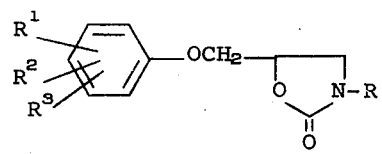

wherein;
R is selected from the group consisting of hydrogen or lower-alkyl having 1 to 4 carbon atoms,
$R^1$ and $R^2$ each are selected from the group consisting of hydrogen, chlorine, bromine, fluorine, lower-alkyl or lower-alkoxy, and
$R^3$ is selected from the group consisting of hydrogen, lower-alkyl, chlorine, bromine or fluorine and (b) an acceptable carrier therefor.

10. The pharmaceutical composition of claim 9 wherein the phenoxymethyl-2-oxazolidinone is metaxalone.

11. A composition of claim 9 in the form of a tablet, aqueous or oily suspension, dispersible powder or granules, emulsion, hard or soft capsule, syrup or elixir.

12. A composition of claim 9 in the form of a food premix for administration to animals.

13. A method for therapy against inflammatory conditions in mammals which comprises administering to said mammals a therapeutically effective amount of an anti-inflammatory composition comprised of the composition of claim 9.

* * * * *